(12) United States Patent
Albean

(10) Patent No.: US 10,485,706 B2
(45) Date of Patent: Nov. 26, 2019

(54) ELECTRONIC HEARING PROTECTOR WITH SWITCHABLE ELECTRICAL CONTACTS

(71) Applicant: 3M INNOVATIVE PROPERTIES COMPANY, St. Paul, MN (US)

(72) Inventor: David L. Albean, Indianapolis, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 16/328,049

(22) PCT Filed: Aug. 24, 2017

(86) PCT No.: PCT/US2017/048470
§ 371 (c)(1),
(2) Date: Feb. 25, 2019

(87) PCT Pub. No.: WO2018/044689
PCT Pub. Date: Mar. 8, 2018

(65) Prior Publication Data
US 2019/0201245 A1    Jul. 4, 2019

Related U.S. Application Data

(60) Provisional application No. 62/380,581, filed on Aug. 29, 2016.

(51) Int. Cl.
*A61F 11/06* (2006.01)
*A61F 11/08* (2006.01)
(Continued)

(52) U.S. Cl.
CPC ............ *A61F 11/08* (2013.01); *H04R 1/1016* (2013.01); *H04R 1/1025* (2013.01);
(Continued)

(58) Field of Classification Search
CPC ..... A61F 11/08; H04R 1/1016; H04R 1/1025; H04R 1/1041
See application file for complete search history.

(56) References Cited

U.S. PATENT DOCUMENTS 4,945,300 A    7/1990  Sato
5,028,806 A    7/1991  Stewart
(Continued)

FOREIGN PATENT DOCUMENTS

CN    201497947    6/2010
CN    102141940    8/2011
(Continued)

OTHER PUBLICATIONS

International Search report for PCT International Application No. PCT/US2017/048470 dated Oct. 18, 2017, 5 pages.

*Primary Examiner* — Simon King
(74) *Attorney, Agent, or Firm* — Katherine M. Scholz; Dena M. Ehrich

(57) ABSTRACT

A battery-powered electronic device, such as an electronic hearing protector (100) includes a housing (113) enclosing the battery and an electronics assembly powered by the battery, the electronics assembly comprises a processor controlled by updatable software. The device further includes a first electrical contact (119*a*) that is a ground line; a second electrical contact (119*b*) that is a data programming line in a first state, and that is a charging voltage line in a second state; and a third electrical contact (119*c*) that is a clock line in a first state, and that is a charge enable line in the second state. The first, second and third electrical contacts (119*a*-*c*) are accessible from outside the housing (113). A switch enclosed by the housing (113) changes the second electrical contact (119*b*) between the first state and the second state.

13 Claims, 7 Drawing Sheets

(51) Int. Cl.
   *H04R 25/00*      (2006.01)
   *H04R 1/10*       (2006.01)
   *A61F 11/14*      (2006.01)
(52) U.S. Cl.
   CPC ......... *H04R 1/1041* (2013.01); *H04R 25/556* (2013.01); *A61F 2011/145* (2013.01); *H04R 2225/31* (2013.01)

(56) References Cited

U.S. PATENT DOCUMENTS

| | | | |
|---|---|---|---|
| 5,097,384 | A | 3/1992 | Sunano |
| 5,459,671 | A | 10/1995 | Duley |
| 5,841,996 | A | 11/1998 | Nolan |
| 5,889,381 | A | 3/1999 | Wakefield |
| 5,966,723 | A | 10/1999 | James |
| 6,212,507 | B1 | 4/2001 | Hwang |
| 6,286,127 | B1 | 9/2001 | King |
| 6,625,731 | B1 | 9/2003 | Plourde |
| 7,096,165 | B2 | 8/2006 | Pantenburg |
| 7,434,089 | B2 | 10/2008 | Smith |
| 7,656,120 | B2 | 2/2010 | Neu |
| 7,689,815 | B2 | 3/2010 | Moyer |
| 7,733,659 | B2 | 6/2010 | Snider |
| 7,791,226 | B2 | 9/2010 | Paillet |
| 8,344,687 | B2 | 1/2013 | Nishikawa |
| 8,667,314 | B2 | 3/2014 | Yen |
| 8,669,752 | B2 | 3/2014 | Schindler |
| 8,810,058 | B2 | 8/2014 | Albean |
| 8,914,127 | B1 * | 12/2014 | Yan ................. A61N 1/36032 607/57 |
| 2004/0139307 | A1 | 7/2004 | Barnett |
| 2007/0169105 | A1 | 7/2007 | Amberny |
| 2009/0202093 | A1 | 8/2009 | Dannemann |
| 2011/0307733 | A1 | 12/2011 | Tokunaga |
| 2012/0051577 | A1 * | 3/2012 | Christensen ........ H04R 25/556 381/380 |
| 2013/0162209 | A1 | 6/2013 | Lee |
| 2013/0162219 | A1 | 6/2013 | Huang |
| 2014/0015337 | A1 | 1/2014 | Takeuchi |
| 2014/0184165 | A1 * | 7/2014 | Takahashi ............ H01M 10/48 320/134 |
| 2014/0380030 | A1 | 12/2014 | Jain |
| 2015/0139474 | A1 | 5/2015 | Henry |

FOREIGN PATENT DOCUMENTS

| | | |
|---|---|---|
| CN | 103149983 | 6/2013 |
| DE | 102005008246 | 8/2006 |
| EP | 1195951 | 4/2002 |
| EP | 1603008 | 12/2005 |
| JP | 59163619 | 9/1984 |
| JP | 60083161 | 5/1985 |
| JP | 05165985 | 7/1993 |
| JP | 06019042 | 1/1994 |
| JP | 2007-304914 | 11/2007 |
| KR | 20080104835 | 12/2008 |
| KR | 20090011860 | 2/2009 |
| KR | 20110078541 | 7/2011 |
| WO | WO 2000-065455 | 11/2000 |

* cited by examiner

ELECTRONIC HEARING PROTECTOR WITH SWITCHABLE ELECTRICAL CONTACTS

CROSS REFERENCE TO RELATED APPLICATIONS

This application is a national stage filing under 35 U.S.C. 371 of PCT/US2017/048470, filed Aug. 24, 2017, which claims the benefit of Provisional Application No. 62/380,581 filed Aug. 29, 2016, the disclosure of which is incorporated by reference in its/their entirety herein.

FIELD OF INVENTION

The present invention relates to an electronic hearing protector. More specifically, the present invention relates to an electronic hearing protector with switchable electrical contacts.

BACKGROUND

Hearing protection devices are used in a broad range of applications, including industrial, military and recreational activities. One particular type of hearing protectors are in-ear pieces that are configured to fit in a user's ear, and may be similar in size to a hearing aid. Such a hearing protector functions to limit impulsive sounds (such as loud machinery or weaponry) to a safe level for the user.

Because such environments can result in exposure to dirt, mud, water, and other elements, it is important to limit the number of apertures or other openings in such a device while still providing a way to recharge a power source in the device and update any software or settings on the device.

SUMMARY

The present invention provides a battery-powered electronic device with switchable electronic contacts. The switchable electronic contacts provide several advantages. For example, it allows a single contact to be used either as a data programming line or a voltage charging line, depending on the state of the device. This provides benefits such as allowing multiple functions to be accomplished with fewer electrical contacts (or pins) than may otherwise be required. This can result in a more compact device, an important feature when the device is being worn in a user's ear. The device may also be easier to manufacture, more reliable and less susceptible to environmental damage because the reduced contacts and associated number of openings in a device housing. The present disclosure also allows flexibility with technology, allowing software to be easily updated, upgraded or changed in a working environment. For example, if a hearing protector consistent with the present disclosure is worn by a worker during the worker's shift, the worker could have the hearing protector attached to a device that both charges and reprograms or updates the software on the unit while the worker is not working.

In one instance, the present disclosure includes a battery-powered electronic device. The device includes a housing enclosing the battery and an electronics assembly. The electronics assembly is powered by the battery, and the electronics assembly comprises a processor controlled by updatable software. The device further includes a first electrical contact that is a ground line; a second electrical contact that is a data programming line in a first state, and that is a charging voltage line in a second state; and a third electrical contact that is a clock line in a first state, and that is a charge enable line in the second state. The first, second and third electrical contacts are accessible from outside the housing. A switch enclosed by the housing changes the second electrical contact between the first state and the second state.

In some instances, the switch is a multiplexer.

In some instances, the switch is an analog switch.

In some instances, the device comprises no more than three electrical contacts accessible from the exterior of the housing.

In some instances, the switch is controlled by a filtered clock signal.

In some instances, data received on the data programming line updates the software.

In some instances, the device is an electronic hearing protector.

The present disclosure also includes a method of updating software on a battery-powered electronic device. The method includes providing a battery-powered electronic device. The device includes a housing enclosing the battery and an electronics assembly. The electronics assembly is powered by the battery. The electronics assembly comprises a processor controlled by updatable software. The device further includes a first electrical contact that is a ground contact; a second electrical contact that it is a data programming line in a first state, and that is a voltage charging line in a second state; and a third electrical contact that is a clock line in a first state, and that is a charge enable line in the second state. The first, second and third electrical contacts are accessible from outside the housing. A switch enclosed by the housing changes the second electrical contact between the first state and the second state. The method further includes transmitting a software update to the processor through the second electrical contact when the second electrical contact is in the second state.

In some instances, the switch is a multiplexer.

In some instances, the switch is an analog switch.

In some instances, the device comprises no more than three electrical contacts.

In some instances, the switch is controlled by a filtered clock signal.

In some instances the device is an electronic hearing protector.

BRIEF DESCRIPTION OF THE DRAWINGS

The invention may be more completely understood in consideration of the following detailed description of various embodiments of the invention in connection with the accompanying drawings, in which.

It is to be understood that the embodiments may be utilized and structural changes may be made without departing from the scope of the invention. The figures are not necessarily to scale. Like numbers used in the figures refer to like components. However, it will be understood that the use of a number to refer to a component in a given figure is not intended to limit the component in another figure labeled with the same number.

DETAILED DESCRIPTION

Figure 1:
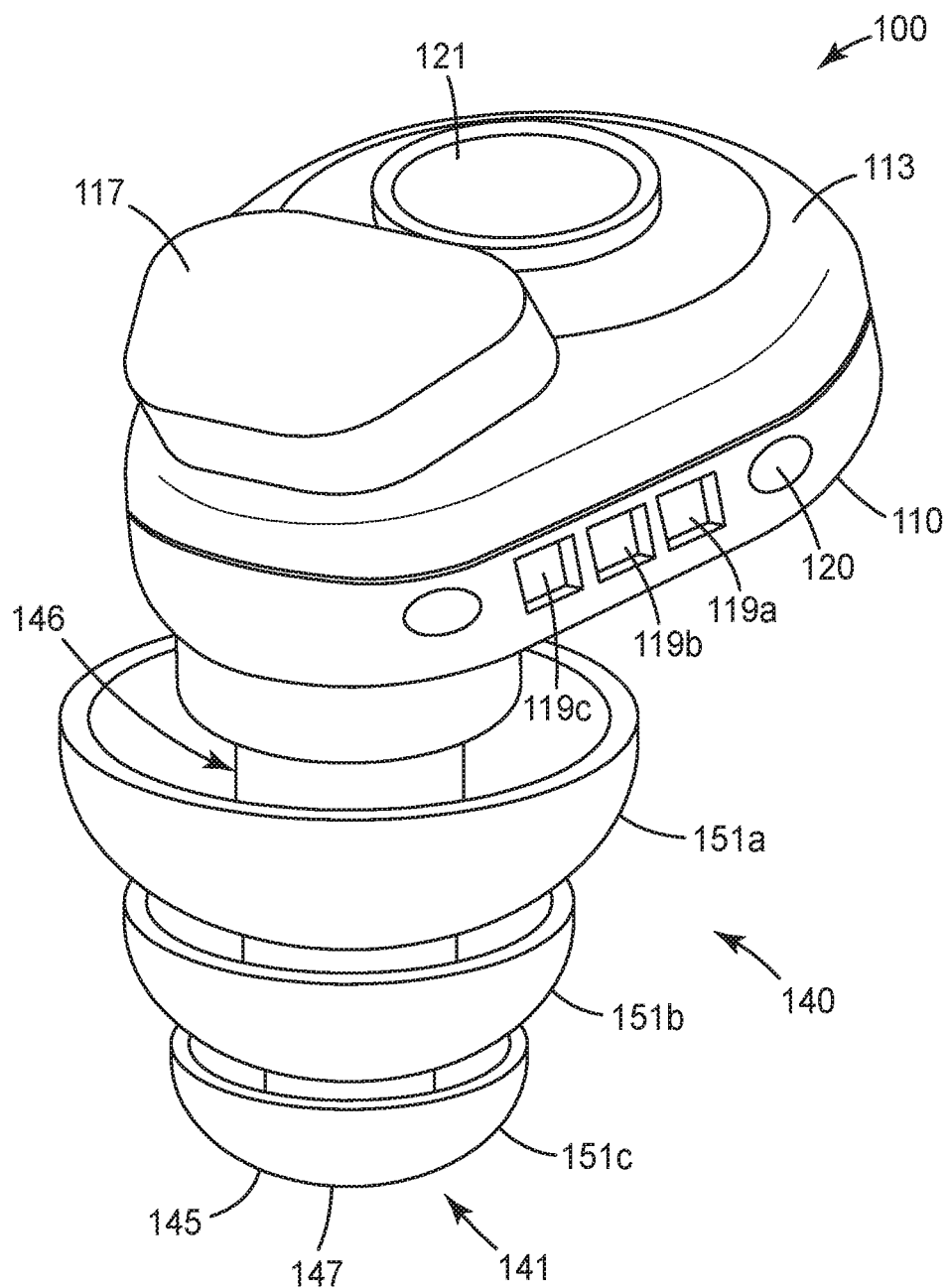
FIG. 1 is an exemplary electronic hearing protection device.

FIG. 1 is an exemplary electronic hearing protection device 100. An exemplary electronic hearing protection device 100 is typically suitable for fitting into a human ear. By an electronic hearing protection device 100 is means a device that substantially prevents ambient airborne sound from directly entering the ear canal, and that includes electronic components that receive ambient airborne sound, convert the sound to electronic signals, process the electronic signals, convert the processed electronic signals into processed sound, then emit the processed sound through a speaker port.

As shown in FIG. 1, device 1 includes two major components: eartip 140 and earpiece body 110. Earpiece body 110 is configured (i.e., shaped and sized) to fit into the concha of a human user's ear and is configured to receive sound, to perform appropriate signal processing and to emit processed sound through a speaker port.

Eartip 140 is configured (i.e., is shaped and sized and is comprised of a material of suitable softness) to fit into the ear canal of the user's ear (which terminology broadly denotes that at least a portion of eartip 140 fits into an outward portion of the ear canal and does not imply that the entirety of eartip 140 must be fitted into the ear canal). Eartip 140 is detachably attached to earpiece body 110 so that eartip 140 can be removed and cleaned or replaced if desired. Eartip 140 comprises a through-passage 141. By through-passage is meant that passage 141 extends through eartip 140 from outward end 146 to inward end 147 and allows the passage of airborne sound therethrough. In at least some embodiments, through-passage 141 is an internal through-passage, meaning that throughout all of its length, passage 141 is radially surrounded by material of eartip 140 (rather than being e.g. a groove or channel that is open to a radially outermost surface of eartip 140). Through-passage 141 (which may be at least generally aligned with a long axis of eartip 140) comprises a first, sound-receiving opening that is acoustically mated to a speaker port of earpiece body 110, and a second, sound emitting opening 145 that faces toward the inner ear of the user, so that processed sound that is emitted from the speaker port can be transmitted through internal through-passage 141 and directed therefrom toward the inner ear of the user.

The fitting of at least a portion of eartip 140 into at least a portion of the ear canal externally occludes the ear canal. By externally occludes is meant that at least some radially outward surfaces (e.g., surfaces 151) of the eartip are in sufficient contact with portions of the walls of the ear canal to substantially prevent ambient airborne sound from traveling along the ear canal in a space otherwise existing between the eartip and the ear canal walls so as to reach the inner ear. However, eartip 140 alone may not completely occlude the ear canal, because through-passage 141 might allow ambient airborne sound to travel therethrough to reach the inner ear unless measures are taken to prevent this. Accordingly, the presence of earpiece body 110 (to which eartip 40 is attached) serves to internally occlude eartip 40. By internally occludes is meant that earpiece body 110 substantially prevents ambient airborne sound from entering first, sound-receiving opening 142 of eartip 140 while still allowing processed airborne sound to enter opening 142, as discussed in detail later herein.

The combination of the external occlusion of the ear canal achieved by eartip 140 and the internal occlusion of eartip 140 achieved by earpiece body 110 can provide excellent overall occlusion of the ear canal and can thus achieve a desired NRR (Noise Reduction Rating). Thus as disclosed herein, earpiece body 110 performs two separate functions, one electronic and one physical. That is, earpiece body 110 does not merely perform electronic processing (e.g., so-called level-dependent processing that allows high intensity sounds to be electronically reduced while low intensity sounds can be passed through or even amplified); it also provides a physical barrier that ensures that entry of ambient airborne sound into the through-passage of the eartip is sufficiently prevented so that a desirably high NRR can be achieved, as discussed in detail herein.

An exemplary earpiece body 10 is shown in FIG. 1. Earpiece body 110 comprises a housing 113 which may be comprised of e.g. a molded polymeric material. In some embodiments, housing 113 may be formed by the mating together of two major housing parts, e.g. inward and outward major housing parts. Housing 113 is hollow so as to at least partially define interior space which may contain any suitable electronic components, one or more internal batteries, and so on. It will be appreciated that since housing 113 serves to protect various electronic components forming an electronic assembly, a resiliently deformable and/or compressible material as may be used for eartip 140, may not be suitable for housing 113. That is, in at least some embodiments, housing 113 may be comprised of a rigid material. In various embodiments, housing 113 may be comprised of an organic polymeric material (e.g., a thermoplastic injection-molding resin) with a hardness of at least about 70, 80, 90 or 100 on a Shore A scale.

Earpiece body 110 (e.g., housing 113 thereof) may comprise an internal battery (not shown in any Figure), a microphone 117 for receiving ambient airborne sound and for converting the received sound to electronic signals, and an electronics assembly (also not shown) for processing the electronic signals, and a speaker (not shown) for transducing the processed signals into airborne processed sound. The electronics assembly broadly encompasses any suitable components that may be desired to be used, e.g. one or more digital signal processors, analog-digital and/or digital-analog converters, data storage units, inductors, capacitors, resistors, and so on, whether such components are discrete components (e.g. mounted on a circuit board) or are provided as part of an integrated circuit. The electronics assembly is powered by the battery enclosed by the housing.

The electronics assembly includes a processor controlled by updatable software initially programmed onto the processor during the manufacturing process. The software can be updated or reprogrammed at a later time as described herein. The housing includes also includes three or more electrical contacts (three such contacts are shown as 19a, 19b, and 19c in FIG. 1) by which an internal battery of device 100 can be recharged, and/or to allow communication with an external appliance (e.g. for configuring or programming device 100). One or more physical alignment features (e.g., sockets or protrusions) 120 may be provided to aid in aligning earpiece body 110 with a recharging unit and/or an external appliance.

In come configurations, a first electrical contact 119a is a ground line. A second electrical contact 119b is a data programming line in a first state and that is a charging voltage line in a second state. A third electrical contact is a clock line in a first state, and is a charge enable line in the second state.

The first electrical contact 119a, second electrical contact 119b, and third electrical contact 119c are accessible from outside the housing. A switch enclosed by the housing changes the second electrical contact between a first state and a second state. In some instances, the switch is a multiplexer. In some instances, the switch is an analog switch. In some instances, the device comprises no more than three electrical contacts accessible from the exterior of the housing. Because the present disclosure provides for a small number of electrical contacts, it can provide benefits such as allowing multiple functions to be accomplished with fewer electrical contacts (or pins) than may otherwise be required. This can result in a more compact device, an important feature when the device is being worn in a user's ear. The device may also be easier to manufacture, more reliable and less susceptible to environmental damage because the reduced contacts and associated number of openings in a device housing.

In some instances, the internal switch governing the state for the second electrical contact is controlled by a filtered clock signal. In some instances, the data received on the data programming line updates the software. The data received on the data programming line may also configure (i.e., update or changes settings) on the software on the processor. When the second electrical contact is in a first state such that the device is receiving data for programming, a clock signal is provided on the third electrical contact. The clock signal on the third electrical contact is filtered to govern the state for the switch tied to the second electrical contact during programming.

One or more external switches 121 (of any suitable type, e.g. a touch-sensitive switch) may be provided to perform any desired function (e.g., turning the device on and off, switching between settings, increasing or decreasing volume, attenuation/gain, or any other parameter, and so on). That is, the term external switch is used broadly to encompass any mechanism by which a user can vary any electronic operating variable of device 1 between two or more settings through physical interaction with the device, whether in discrete steps or in a continuous manner. If external switch 121 is a touch-sensitive switch, it may be of any suitable type, operating by any suitable mechanism (e.g., it might be an electrically-operating switch such as a capacitive, resistive, or piezo switch; or, it might be a mechanical switch).

A first general measure is that housing 113 of earpiece body 110 can be configured so as to minimize the entry of ambient airborne sound into interior space 22 of earpiece body 10. This may be done by e.g. minimizing the number and size of any through-openings in housing 11. In particular embodiments, device 100 can include a rechargeable battery, such as a lithium ion battery, which eliminates the need for a battery door (with the term door being used broadly to encompass any kind of opening, cover, etc., hinged or otherwise) through which a replaceable battery could be removed. The ordinary artisan will appreciate that such a battery door, even when closed, can comprise e.g. slit leaks that might allow ambient airborne sound to enter the interior space of earpiece body 110. Thus in specific embodiments, housing 11 of earpiece body 10 of device 1 does not comprise any battery door. Beyond this, housing 113, if made e.g. of two major housing parts that are mated together (assembled) to form housing 113, may be configured so as to not be disassemblable by a user (e.g., to replace a battery) in ordinary use of device 100. That is, such major housing parts may be configured to fit together with very close tolerances (and/or to provide a circuitous path through junction therebetween), and/or the junction between such major housing parts may comprise any suitable gaskets, sealants, adhesives, and the like, as can e.g. provide a tight seal therebetween. Such provisions can further minimize the entry of ambient airborne sound into the interior space of earpiece body 110.

Still further, the size and number through-openings in housing 113 that might be necessary e.g. to accommodate a component such as e.g. an electrical connector, a switch, a microphone, and so on, can be designed to be minimized to obtain the advantages discussed herein. Further, in similar manner as described with regard to the mating of major housing parts, any suitable gasket, sealant, adhesive, or the like, can be used in mounting any such component to a through-opening in housing 113. Such arrangements can further minimize the amount of ambient airborne sound that is able to penetrate into the interior space of earpiece body 110.

The collective effect of such arrangements in minimizing the number and/or magnitude of e.g. air leaks in housing 110 may be gauged by the determination of an Ingress Protection Rating for housing 110 and/or for any component thereof. Such a Rating can be determined in accordance with Publication 60529 (Classification of Degrees of Protection Provided by Enclosures) as specified in 2013 by the International Electrotechnical Commission. (It will be appreciated that for purposes of such testing, a speaker port of housing 110 can be sealed.) An Ingress Protection Rating (also known as an IP Code or International Protection Rating) provides two numerical parameters. The first parameter denotes the ability of an enclosure to resist the penetration of solid objects, and has a scale of 0-6, with e.g. 0 indicating no protection and 6 indicating protection from ingress of dust. The second parameter denotes the ability of an enclosure to resist the penetration of liquid, and has a scale of 0-7, with e.g. 0 indicating no protection and 7 indicating protection from ingress of water upon immersion in water to a depth of between 15 centimeters and 1 meter. In various embodiments, housing 110 of device 1 may exhibit an Ingress Protection Rating of at least IP56, IP57, or IP66. In specific embodiments, housing 110 may exhibit an Ingress Protection Rating of IP67.

In the discussions herein, various devices, components and arrangements have been characterized as e.g. "substantially preventing" the passing of airborne sound waves. It will be understood that such terminology does not require that such a device, component or arrangement necessarily provide an absolute barrier to airborne sound. Rather, the only requirement signified by this terminology is that all such components and arrangements collectively provide sufficient barrier properties to airborne sound that device 1, comprising eartip 40 and earpiece body 10 as disclosed herein, is capable of functioning as disclosed herein. An electronic hearing protection device 100 consistent with the present disclosure may have additional features as described in further detail in United States Published Patent Application 2015/00139474 to Henry.

Figure 2:
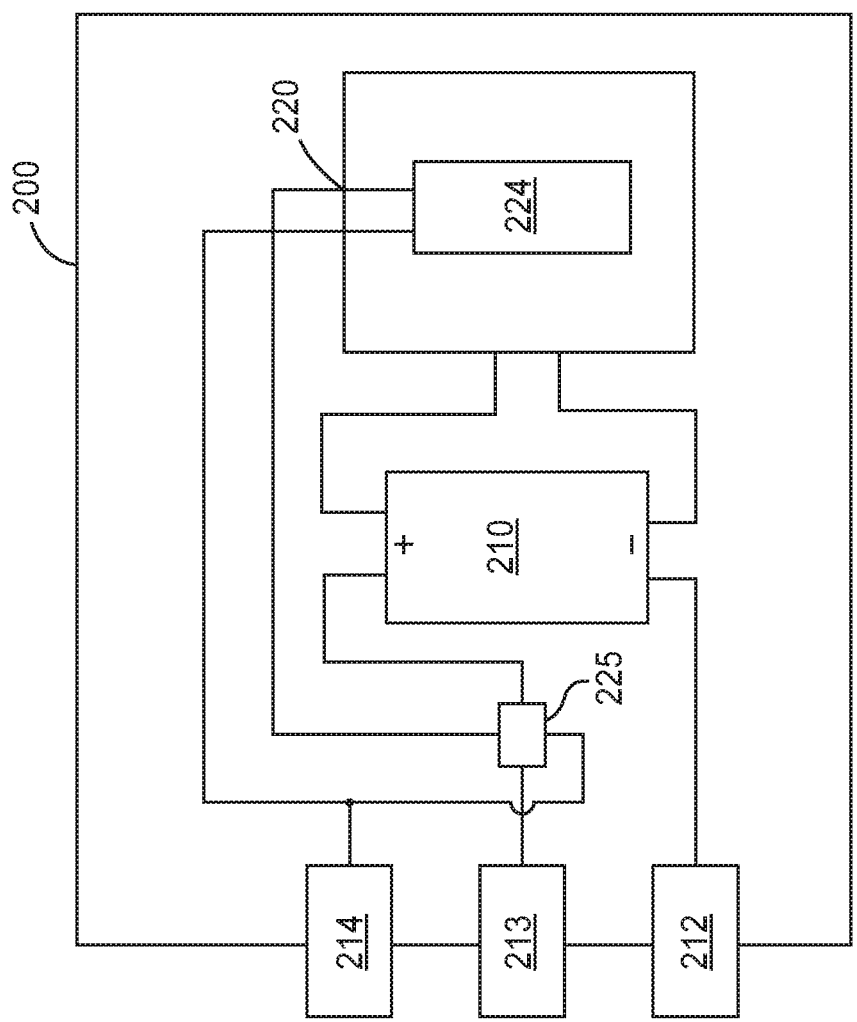
FIG. 2 is a block diagram of an exemplary battery powered electronic device.

FIG. 2 is a block diagram of an exemplary battery powered electronic device 200. While a battery powered electronic device has been discussed in the present disclosure in the context of an electronic hearing protection device, the present disclosure applies more broadly to battery powered electronic devices. FIG. 2 is a block diagram of an exemplary battery powered electronic device 200 consistent with the present disclosure.

Housing 200 contains electronics assembly 220. Electronics assembly 220 broadly encompasses any suitable components that may be desired to be used, e.g. one or more digital signal processors, analog-digital and/or digital-analog converters, data storage units, inductors, capacitors, resistors, and so on, whether such components are discrete components (e.g. mounted on a circuit board) or are provided as part of an integrated circuit. Electronics assembly includes processor 224. Processor 224 is controlled by updatable and/or configurable software. Components in electronics assembly 220 are powered by internal battery 210.

First electrical contact 212 is a ground line and is electrically connected to the battery 210 negative. Second electrical contact 213 can switch between a first state and a second state. Switch 225 switches second electrical contact 213 between a first state and a second state. When electrical contact 213 is in a first state, electrical contact 213 is a data programming line. When electrical contact 213 is a data programming line, an external device can be connected to electrical contact 213 and electrical contact 212 to change a configuration in the software on the processor, update the software on the processor, or reprogram the software on the processor. During programming, a data signal is applied to electrical contact 213 and a clock signal is applied to electrical contact 214. The clock signal applied to electrical contact 214 is filtered to derive a control signal for switch 225. When electrical contact 213 is in a second state, electrical contact 213 is a voltage charging line. When electrical contact 213 is a voltage charging line, an external device can be connected to electrical contact 213 and electrical contact 212 to recharge battery 210. When battery 210 is being recharged, electrical contact 214 may be left open.

Switch 225 can operate in a variety of ways. In one instance, switch 225 can be a multiplexer and be controlled by input from processor 224. In another instance, switch 225 may be an analog switch. In one instance (as illustrated), switch 225 is controlled by a filtered clock signal.

Third electrical contact 214 is also accessible from the exterior of housing 200. Third electrical 214 contact can receive a clock signal when the device is being programmed (in a first state) or may be left open or connected to a ground when battery 210 is being charged (in a second state). In some instances, third electrical contact 214 may be switched between a first state and a second state by a switch, and in other instances, it may be switched between a first state and a second state through a network discrete components. Other methods for implementing the switching described herein will be apparent to one of skill in the art upon reading the present disclosure, and are within the scope of the present disclosure.

Figure 3:
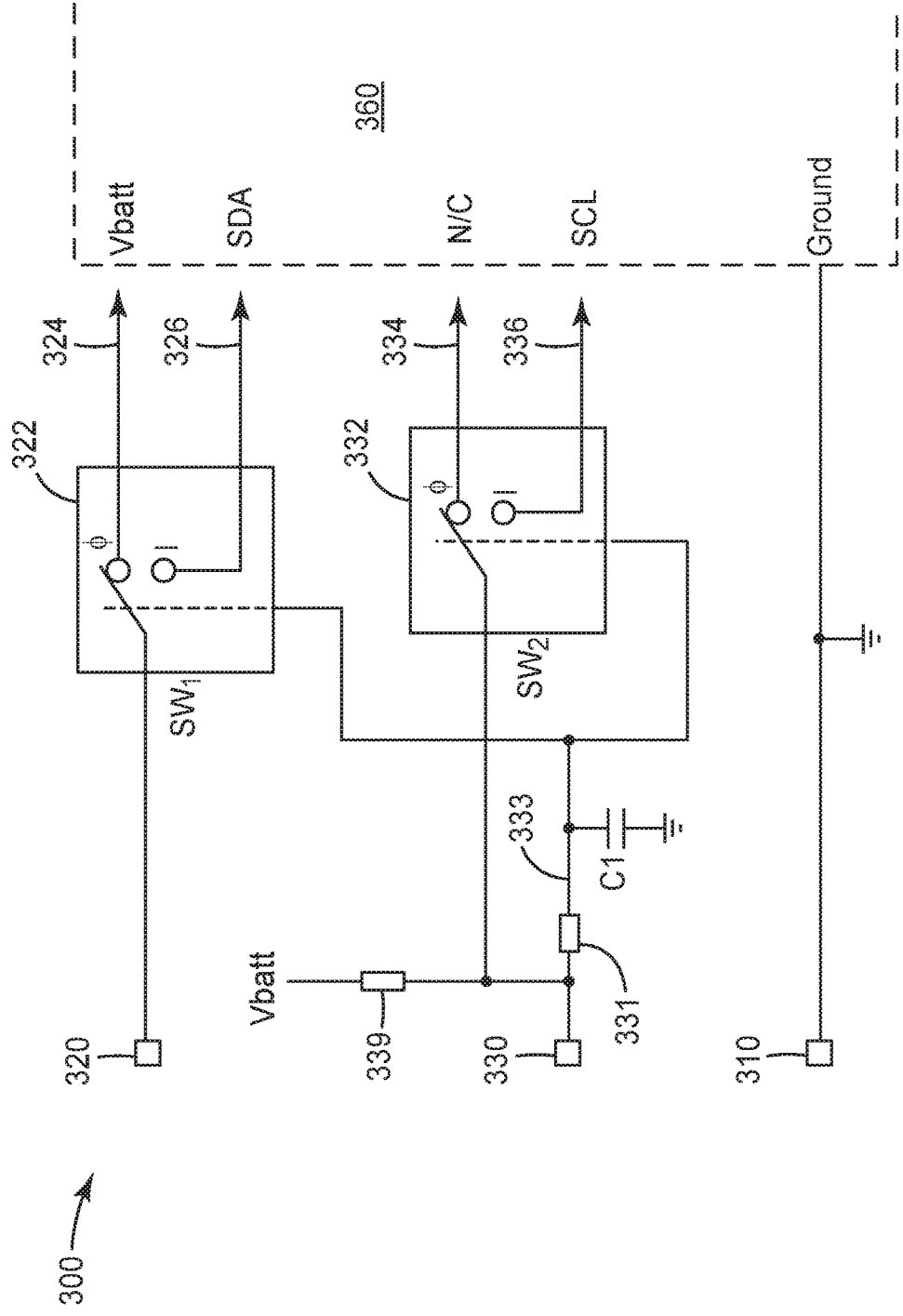
FIG. 3 is an exemplary schematic diagram of the electrical components in a battery powered electronic device.

FIG. 3 is an exemplary schematic diagram 300 of the electrical contacts and related switches that interface with components of the electronic assembly in a battery powered electronic device. While there are multiple ways to implement the present disclosure, FIG. 3 illustrates one way of doing so.

First electrical contact 310 is a ground contact and is tied to a common ground throughout the electronic device.

Second electrical contact 320 and third electrical contact 330 are multi-state electrical contacts, and are switched between a first state and a second state by switch 322 and switch 332, respectively.

When second electrical contact 320 and third electrical contact 330 are each in a first state, the device is receiving data that can be used to configure, reprogram, or update a processor that is part of electronic assembly 360. In this first state, the voltage level on electrical contact 330 is pulled up to a positive voltage level by the connection to resistor 339 and the battery positive, causing switch 322 and switch 332 to select lines 326 and 336, respectively. When switch 332 selects line 336, electrical contact 330 is tied to clock line 336. During this first state, a programming device provides a clock signal as input to electrical contact 330, and thus clock line 336. While the clock input on electrical contact 330 will oscillate between a positive and negative voltage, the network (or filter) of resistor (R2) 331 and capacitor (C1) 333 ensure that the control signal for each of switch 322 and switch 332 is held high so that neither switch opens during programming. In this way, the signal applied to the third electrical contact can provide a select signal to switches 322 and 332 to cause them to select lines 326 and 336 respectively. During this first state, a data signal is transmitted over electrical contact 320 to reprogram, update, or configure the processor.

When second electrical contact 320 and third electrical contact 330 are each in a second state, the device is receiving input voltage to recharge the internal battery. During the second state (or the recharging process) a positive voltage is applied to second electrical contact 320 and third electrical contact 330 is grounded (along with first electrical contact 310). When third electrical contact 330 is tied to ground, the input to switches 322 and 332 is sufficiently low to cause each of switches 322 and 332 to open, or to select lines 324 and 334, respectively. When second electrical contact 320 is connected to line 324, it is tied to the battery positive and provides power to recharge the internal battery in the device. When third electrical contact 330 is tied to line 334, it is open and thus grounded. This results in the charger or outside device being connected to both ends to the internal battery to charge it.

Figure 4:
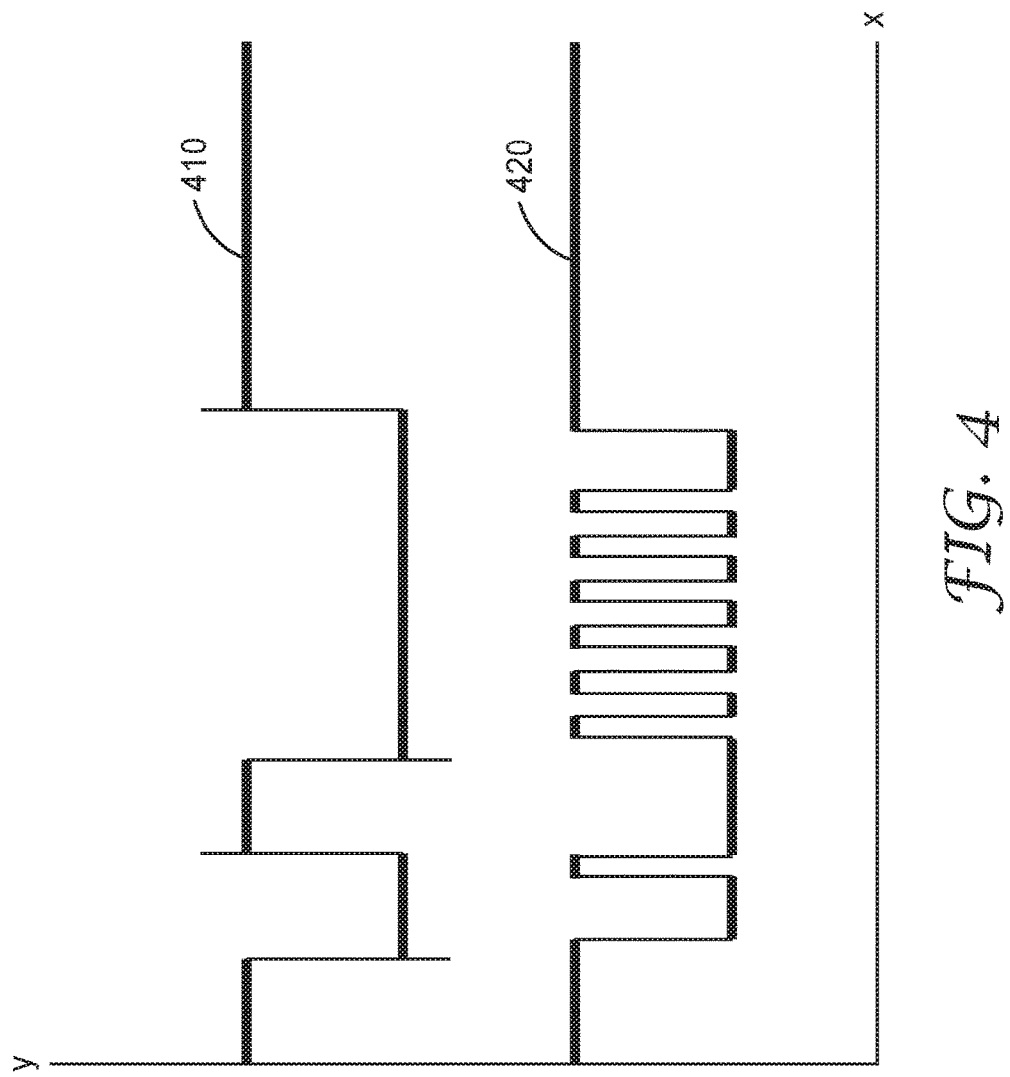
FIG. 4 shows voltage level of signals over time applied to electrical contacts during a programming state for a battery powered electronic device.

FIG. 4 shows voltage level of signals over time applied to electrical contacts during a programming state for a battery powered electronic device. In the graph shown in FIG. 4, the x-axis represents time. The y-axis represents voltage. Signal 420 is a clock signal, and is exemplary of a signal that may be present on a third electrical contact when the third electrical contact is in a first state (or a data input state). Signal 410 is a data signal, and is exemplary of a signal that may be present on a second electrical contact when the second electrical contact is in a first state. Both signal 410 and signal 420 have a peak to peak voltage of about 1.8 volts.

Figure 5:
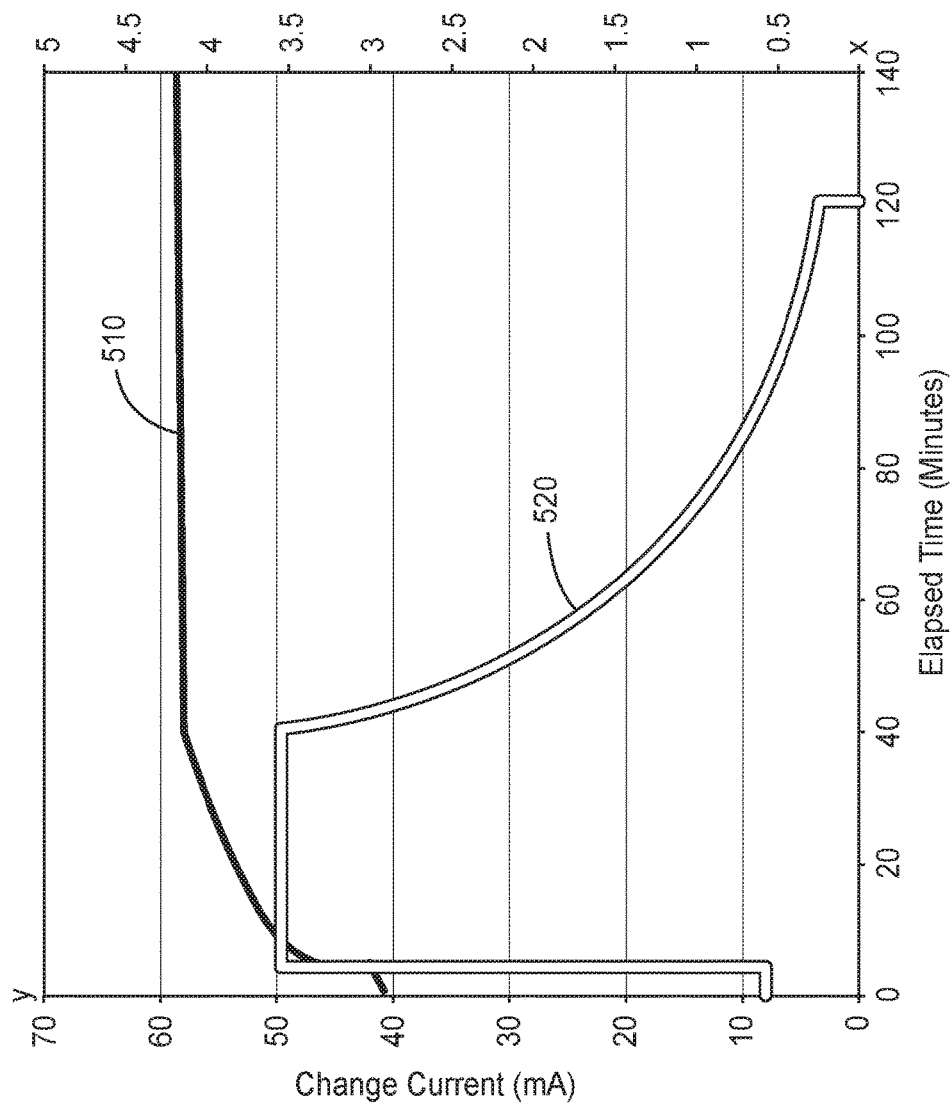
FIG. 5 is a diagram of voltage levels over time as a battery powered electronic device charges.

FIG. 5 is a diagram of voltage levels over time as a battery powered electronic device charges. In the graph shown in FIG. 5, the x-axis represents elapsed time (in minutes) from the beginning of a cycle of charging an internal battery in a battery powered electronic device consistent with the present disclosure. The y-axis as shown in FIG. 5 represents on the left side, charge current in milliAmps (mA), and on the right side, voltage level of the internal battery in Volts (V). Current line 520 illustrates exemplary current levels on a second electrical contact when the second electrical contact is in a second state (voltage charging state). During charging, a constant current of 50 mA is applied to the internal battery for the required time, for example, about 40 minutes, then the current tapers as the voltage in the internal battery is increasing to its final, full charge value. Voltage line 510 shows a gradual increase from a decreased voltage level (approximately 2.9 V) to a fully charged voltage level of approximately 4.2 V over a period of about 120 minutes.

Voltage and current levels for charging a battery will vary dependent on the device power needs, and the battery chosen to suit those needs.

Figure 6:
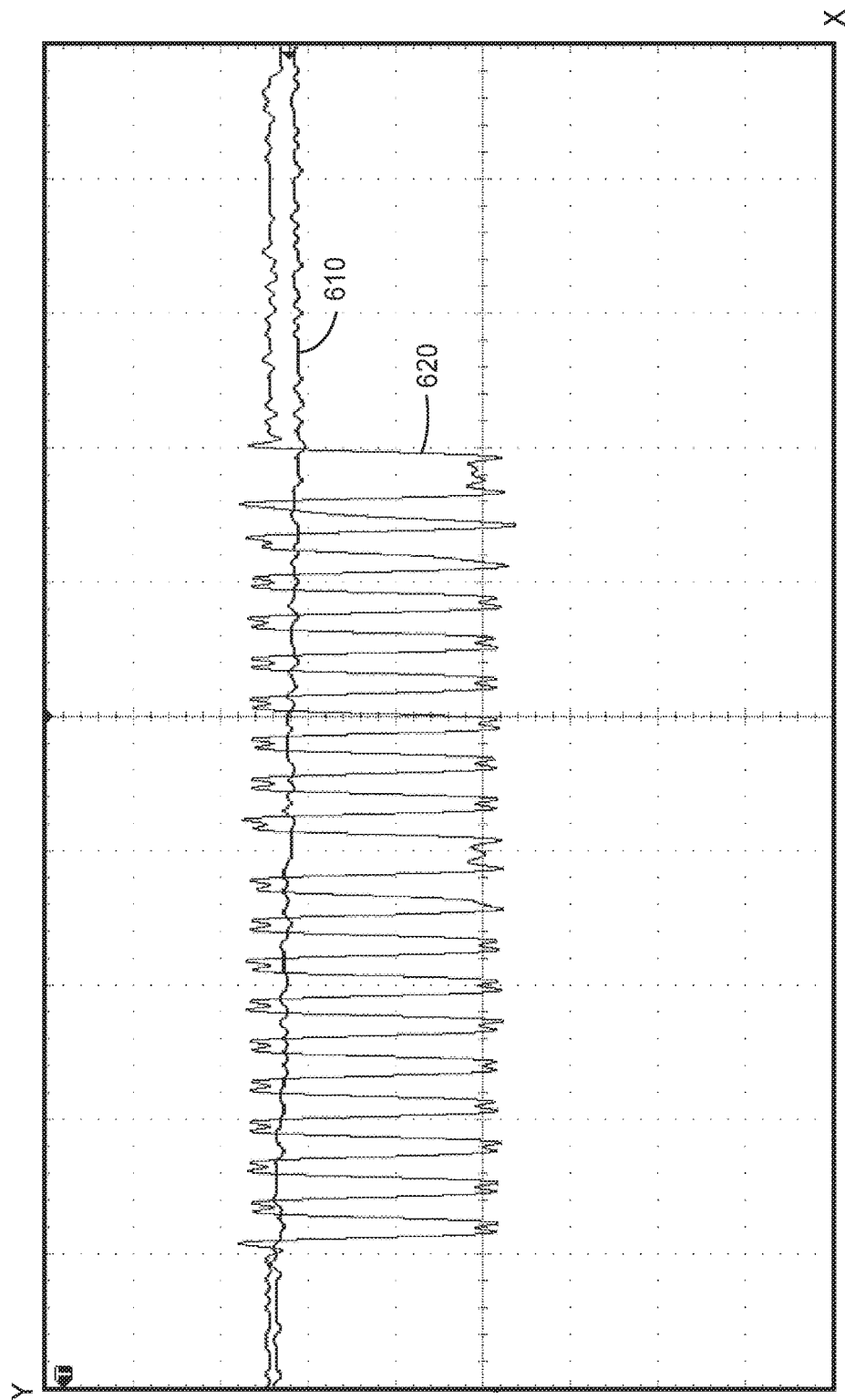
FIG. 6 is a diagram showing voltage levels for a clock signal and a filtered clock signal over time.

FIG. 6 is a diagram showing voltage levels for a clock signal 620 and a filtered clock 610 signal over time. Clock signal 620 shows more cycles and is a magnified version clock signal 420 in FIG. 4. In the graph shown in FIG. 6, the x-axis represents time, with the divisions on the x-axis representing about 25 microseconds per division. The y-axis represents voltage, with each division representing about 0.5 volts. Signal 620 is a clock signal, and is exemplary of an input clock signal received on a third electrical contact when that contact is in a first (data input) state. Signal 610 is derived by filtering signal 620 with an RC filter, and is exemplary of a signal that might be used as a control signal for switches 322 and 332 in FIG. 3. Filtering the clock input signal 620 allows the control input to switches 322 and 332 to stay high even as the clock signal is toggling.

EXAMPLE

Figure 7:
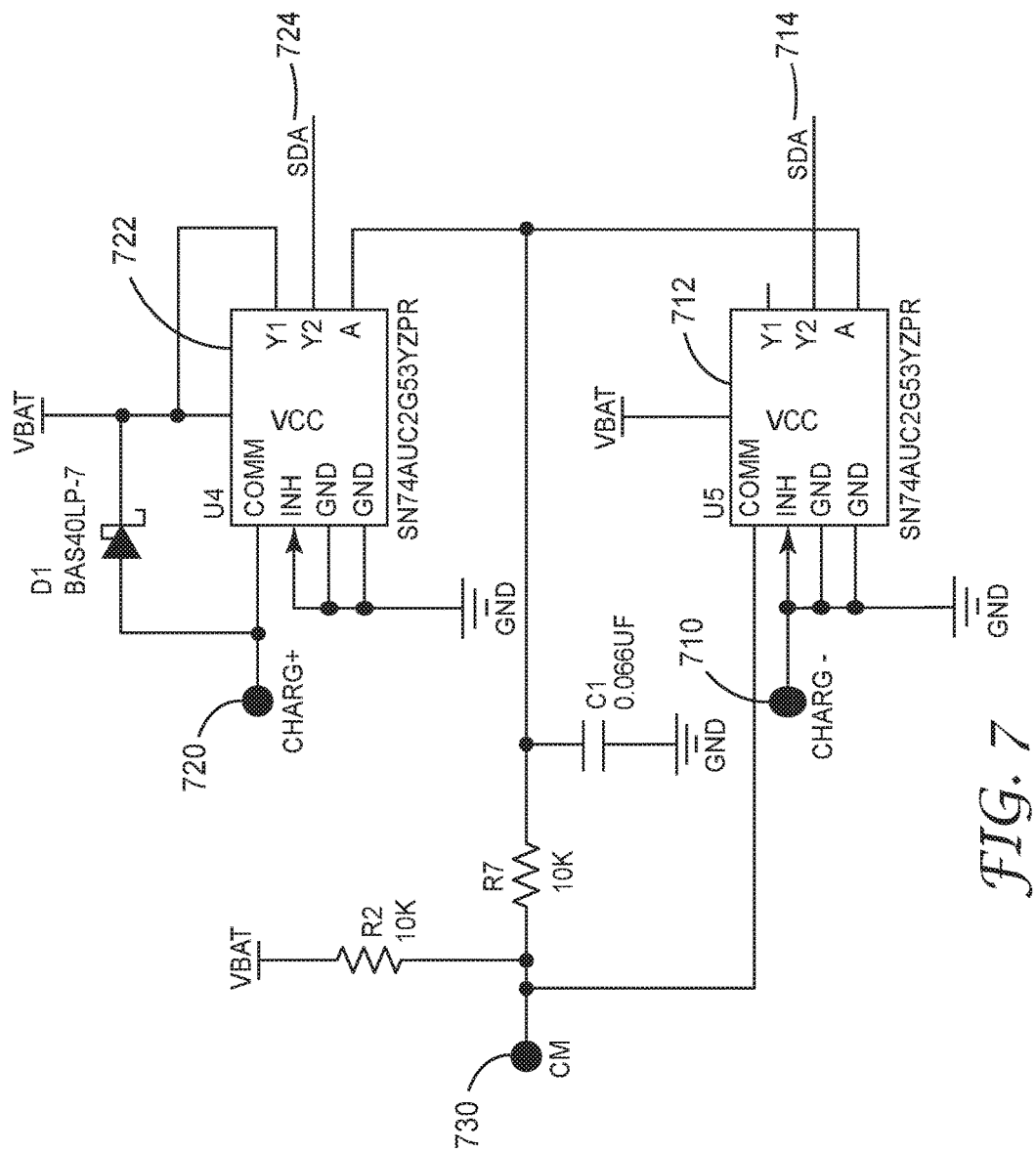
FIG. 7 is an exemplary schematic diagram of the electrical components in a battery powered electronic device.

FIG. 7 illustrates a prophetic example in the form of a schematic diagram generated by a circuit simulation program showing how electrical components in a battery powered electronic device may be selected and connected consistent with the scope of the present disclosure.

In FIG. 7, three electrical contacts are multiplexed in a way such that a first state enables programming while a second state enables charging of the internal battery in the device.

The three electrical contacts, CHARG– 710, CHARG+ 720 and CM 730, are switchable between a first and second state to allow either reprogramming or charging. This is accomplished with two solid state single pole, double throw (SPDT) switches 712 and 722. Switches that may be used are, for example, SPDT Analog Switch Part Number SN74AUC2G53YZPR available from Texas Instruments Incorporated, headquartered in Dallas, Tex.

In a first state, when electrical contact CM 730 is left open, the CHARG+ 720 and CM 730 electrical contacts connect the reprogramming signals, SDA 724 and SCL 714, respectively, via switches 722 and 712 to a processor in the device (not shown). Signal SCL 714 is used as a control signal to switches 722 and 712 to select which nodes electrical contacts 710 and 720 are connected to. Signals SDA 724 and SCL 714 normally idle in a high state, and an RC network can be used to insure that the switch control signals (pins D2 in each of switches 712 and 722) do not toggle during reprogramming—they are held high during the reprogramming process.

In a second state, to charge the earpiece, electrical contact CM 730 is grounded (via placement of the device into a charger). Grounding electrical contact CM 730 configures the electrical contacts CHARG+ 720 and CHARG– 730 to charge the battery through the switches 722 and 712, respectively.

Switches 712 and 722 connect the electrical contacts (CHARG+ 720, CM 730, CHARG– 710) as follows to affect charging OR reprogramming:

| Electrical Contact | To charge | To program |
|---|---|---|
| CHARG(+) 720 | VBAT | SDA 724 |
| CM 730 | Ground | SCL 714 |
| CHARG– 710 | Ground | Ground |

Although the methods and systems of the present disclosure have been described with reference to specific exemplary embodiments, those of ordinary skill in the art will readily appreciate that changes and modifications may be made thereto without departing from the spirit and scope of the present disclosure.

In the present detailed description of the preferred embodiments, reference is made to the accompanying drawings, which illustrate specific embodiments in which the invention may be practiced. The illustrated embodiments are not intended to be exhaustive of all embodiments according to the invention. It is to be understood that other embodiments may be utilized and structural or logical changes may be made without departing from the scope of the present invention. The following detailed description, therefore, is not to be taken in a limiting sense, and the scope of the present invention is defined by the appended claims.

Unless otherwise indicated, all numbers expressing feature sizes, amounts, and physical properties used in the specification and claims are to be understood as being modified in all instances by the term "about." Accordingly, unless indicated to the contrary, the numerical parameters set forth in the foregoing specification and attached claims are approximations that can vary depending upon the desired properties sought to be obtained by those skilled in the art utilizing the teachings disclosed herein.

As used in this specification and the appended claims, the singular forms "a," "an," and "the" encompass embodiments having plural referents, unless the content clearly dictates otherwise. As used in this specification and the appended claims, the term "or" is generally employed in its sense including "and/or" unless the content clearly dictates otherwise.

Spatially related terms, including but not limited to, "proximate," "distal," "lower," "upper," "beneath," "below," "above," and "on top," if used herein, are utilized for ease of description to describe spatial relationships of an element(s) to another. Such spatially related terms encompass different orientations of the device in use or operation in addition to the particular orientations depicted in the figures and described herein. For example, if an object depicted in the figures is turned over or flipped over, portions previously described as below or beneath other elements would then be above or on top of those other elements.

As used herein, when an element, component, or layer for example is described as forming a "coincident interface" with, or being "on," "connected to," "coupled with," "stacked on" or "in contact with" another element, component, or layer, it can be directly on, directly connected to, directly coupled with, directly stacked on, in direct contact with, or intervening elements, components or layers may be on, connected, coupled or in contact with the particular element, component, or layer, for example. When an element, component, or layer for example is referred to as being "directly on," "directly connected to," "directly coupled with," or "directly in contact with" another element, there are no intervening elements, components or layers for example. The techniques of this disclosure may be implemented in a wide variety of computer devices, such as servers, laptop computers, desktop computers, notebook computers, tablet computers, hand-held computers, smart phones, and the like. Any components, modules or units have been described to emphasize functional aspects and do not necessarily require realization by different hardware units. The techniques described herein may also be implemented in hardware, software, firmware, or any combination thereof. Any features described as modules, units or components may be implemented together in an integrated logic device or separately as discrete but interoperable logic devices. In some cases, various features may be implemented as an integrated circuit device, such as an integrated circuit chip or chipset. Additionally, although a number of distinct modules have been described throughout this description, many of which perform unique functions, all the functions of all of the modules may be combined into a single module, or even split into further additional modules. The modules described herein are only exemplary and have been described as such for better ease of understanding.

If implemented in software, the techniques may be realized at least in part by a computer-readable medium comprising instructions that, when executed in a processor, performs one or more of the methods described above. The computer-readable medium may comprise a tangible computer-readable storage medium and may form part of a computer program product, which may include packaging materials. The computer-readable storage medium may comprise random access memory (RAM) such as synchronous dynamic random access memory (SDRAM), read-only memory (ROM), non-volatile random access memory (NVRAM), electrically erasable programmable read-only memory (EEPROM), FLASH memory, magnetic or optical data storage media, and the like. The computer-readable storage medium may also comprise a non-volatile storage device, such as a hard-disk, magnetic tape, a compact disk (CD), digital versatile disk (DVD), Blu-ray disk, holographic data storage media, or other non-volatile storage device.

The term "processor," as used herein may refer to any of the foregoing structure or any other structure suitable for implementation of the techniques described herein. In addition, in some aspects, the functionality described herein may be provided within dedicated software modules or hardware modules configured for performing the techniques of this disclosure. Even if implemented in software, the techniques may use hardware such as a processor to execute the software, and a memory to store the software. In any such cases, the computers described herein may define a specific machine that is capable of executing the specific functions described herein. Also, the techniques could be fully implemented in one or more circuits or logic elements, which could also be considered a processor.

What is claimed is:

1. A battery-powered electronic device, comprising:
   a housing enclosing the battery and an electronics assembly, wherein the electronics assembly is powered by the battery, and wherein the electronics assembly comprises a processor controlled by updatable software;
   a first electrical contact that is a ground line; and
   a second electrical contact that is a data programming line in a first state, and that is a voltage charging line in a second state;
   a third electrical contact that is a clock line in a first state, and that is a charge enable line in the second state;
   wherein the first, second and third electrical contacts are accessible from outside the housing;
   wherein a switch enclosed by the housing changes the second electrical contact between the first state and the second state.

2. The device of claim 1, wherein the switch is a multiplexer.

3. The device of claim 1, wherein the switch is an analog switch.

4. The device of claim 1, wherein the device comprises no more than three electrical contacts accessible from the exterior of the housing.

5. The device of claim 1, wherein the switch is controlled by a filtered clock signal.

6. The device of claim 1, wherein data received on the data programming line updates the software.

7. The device of claim 1, wherein the device is an electronic hearing protector.

8. A method of updating software on a battery-powered electronic device, comprising:
   providing a battery-powered electronic device comprising:
     a housing enclosing the battery and an electronics assembly, wherein the electronics assembly is powered by the battery, and wherein the electronics assembly comprises a processor controlled by updatable software;
     a first electrical contact that is a ground contact; and
     a second electrical contact that it is a data programming line in a first state, and that is a voltage charging line in a second state;
     a third electrical contact that is a clock line in a first state, and that is a charge enable line in the second state;
     wherein the first, second and third electrical contacts are accessible from outside the housing;
     wherein a switch enclosed by the housing changes the second electrical contact between the first state and the second state; and
   transmitting a software update to the processor through the second electrical contact when the second electrical contact is in the first state.

9. The method of claim 8, wherein the switch is a multiplexer.

10. The method of claim 8, wherein the switch is an analog switch.

11. The method of claim 8, wherein the device comprises no more than three electrical contacts.

12. The method of claim 8, wherein the switch is controlled by a filtered clock signal.

13. The method of claim 8, wherein the device is an electronic hearing protector.

* * * * *